(12) United States Patent
Liu et al.

(10) Patent No.: US 10,597,436 B2
(45) Date of Patent: Mar. 24, 2020

(54) ACYLATED INSULIN COMPOUND

(71) Applicant: Eli Lilly and Company, Indianapolis, IN (US)

(72) Inventors: Wen Liu, Carmel, IN (US); Adam Robert Mezo, San Diego, CA (US); Francisco Alcides Valenzuela, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/529,095

(22) Filed: Aug. 1, 2019

(65) Prior Publication Data

US 2019/0345215 A1 Nov. 14, 2019

Related U.S. Application Data

(62) Division of application No. 15/983,167, filed on May 18, 2018, now Pat. No. 10,400,021.

(60) Provisional application No. 62/511,690, filed on May 26, 2017.

(51) Int. Cl.
*A61K 38/28* (2006.01)
*A61K 47/54* (2017.01)
*C07K 14/62* (2006.01)
*A61P 3/10* (2006.01)
*A61K 47/65* (2017.01)
*A61K 38/00* (2006.01)

(52) U.S. Cl.
CPC ............ *C07K 14/62* (2013.01); *A61K 47/542* (2017.08); *A61K 47/65* (2017.08); *A61P 3/10* (2018.01); *A61K 38/00* (2013.01)

(58) Field of Classification Search
None
See application file for complete search history.

(56) References Cited

FOREIGN PATENT DOCUMENTS

| WO | 2005/012347 A2 | 2/2005 |
| WO | 2006/082205 A1 | 8/2006 |
| WO | 2009/022006 A1 | 2/2009 |
| WO | 2014/147141 A1 | 9/2014 |

OTHER PUBLICATIONS

International Search Report of the International Searching Authority pertaining to International Application No. PCT/US2018/033418; International Filing Date: May 18, 2018; dated Aug. 6, 2018.
Written Opinion of the International Searching Authority pertaining to International Application No. PCT/US2018/033418; International Filing Date: May 18, 2018; dated Aug. 6, 2018.

*Primary Examiner* — Julie Ha
*Assistant Examiner* — Kristina M Hellman
(74) *Attorney, Agent, or Firm* — Matthew T. Lord

(57) ABSTRACT

The presently described compounds relate to the treatment of diabetes and/or hyperglycemia. More particularly, the described compounds relate to acylated insulin compounds that lower blood glucose, pharmaceutical compositions containing such compounds, therapeutic uses of such compounds, and an intermediate compound used to make the acylated insulin compounds.

1 Claim, No Drawings

Specification includes a Sequence Listing.

ACYLATED INSULIN COMPOUND

The present invention is in the field of treatment of diabetes and/or hyperglycemia. The invention relates to compounds that lower blood glucose, pharmaceutical compositions containing such compounds and therapeutic uses of such compounds.

Insulin replacement therapy for diabetic patients ideally would parallel as closely as possible the pattern of endogenous insulin secretion in healthy individuals. The physiological demand for insulin may be separated into two phases: (a) a nutrient absorptive phase requiring a pulse of insulin to dispose of the meal-related blood glucose surge, also known as "prandial" insulin, and (b) a post-absorptive phase requiring a sustained delivery of insulin to regulate hepatic glucose output for maintaining optimal fasting blood glucose, also known as a "basal" insulin.

Effective insulin therapy for people with diabetes generally may involve the combined use of two types of exogenous insulin formulations: a rapid-acting, mealtime prandial insulin, and a longer-acting basal insulin administered once or twice daily to control blood glucose levels between meals. One or more characteristics of endogenous insulin that may be desirable to emulate include a binding affinity for the human insulin receptors, preferential binding to the human insulin receptors over the human IGF-1 receptor, phosphorylation of the human insulin receptors, and glucose lowering in the blood.

A desirable exogenous basal insulin should also provide an extended time action—that is, it would control blood glucose levels for at least 12 hours, and preferably for 24 hours or longer, without significant risk of hypoglycemia. Some basal insulins have a duration of action of 24 hours or more. A compound with an extended time-action profile, without significant variations in effectiveness during that time, may lower the risk of nocturnal hypoglycemia and allow greater variability in daily dosing times without increasing a patient's risk of hypoglycemia. Characteristics of an exogenous basal insulin that may be desirable include reduced clearance rate from the bloodstream and chemical stability at multiple concentrations, which could contribute to extended shelf-life stability.

The need exists for alternative treatments for diabetes and/or hyperglycemia in patients in need thereof. Some acylated insulin compounds are known, see, for example, U.S. Pat. Nos. 6,444,641 and 7,615,532, but there is a need for additional alternative treatments. The present invention provides a compound that is useful in treating diabetes, reducing hemoglobin A1c, and reducing blood glucose levels in patients in need thereof. The present compounds are also made using a novel compound, described below.

The present invention includes a compound of the formula (Formula I):

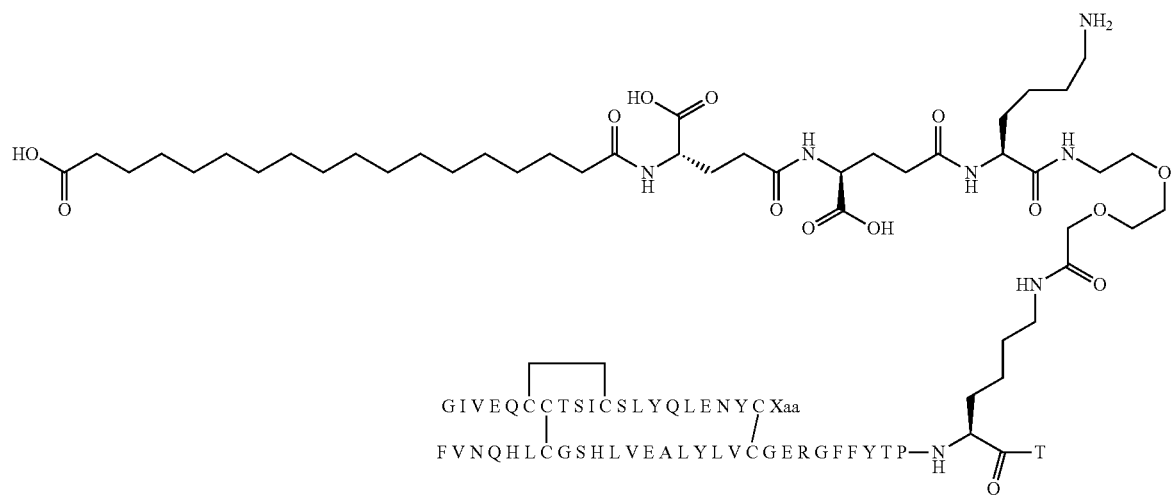

wherein Xaa is the amino acid glycine or asparagine.

The compound of Formula I is an insulin compound consisting of an A-chain with amino acid sequence SEQ ID NO: 1 and a B-chain with amino acid sequence SEQ ID NO: 4 wherein a disulfide bond exists between the cysteine at position 6 of SEQ ID NO: 1 and the cysteine at position 11 of SEQ ID NO: 1, a disulfide bond exists between the cysteine at position 7 of SEQ ID NO: 1 and the cysteine at position 7 of SEQ ID NO: 4, a disulfide bond exists between the cysteine at position 20 of SEQ ID NO: 1 and the cysteine at position 19 of SEQ ID NO: 4, and the lysine at position 29 of the B chain (SEQ ID NO: 4) is chemically modified by formation of an amide bond between the epsilon-amino group of the lysine side-chain and the free carboxylate of AEEA with OH—C18-γGlu-γGlu-Lys-(AEEA)-, where OH—C18 is octadecanedioic acid, γGlu is L-glutamic acid connected through its side-chain gamma carboxyl group, and AEEA is 2-[2-(2-aminoethoxy)ethoxy]acetic acid. The above structure, Formula I, contains the standard single letter amino acid codes for the amino acid residues of the insulin A chain and B chain, with the exception of residue 29 of the B chain, which is lysine, where the structure of that amino acid residue has been expanded.

The present compounds further include Compound 12, which has the structure of Formula I and wherein Xaa is the amino acid glycine. The present compounds further include Compound 19, which has the structure of Formula I and wherein Xaa is the amino acid asparagine.

The present application also provides a pharmaceutical composition comprising the compound of Formula I, Compound 12, or Compound 19 and one or more pharmaceutically acceptable excipients. The present application further provides a method of treating diabetes in a patient comprising administering to a patient in need thereof an effective amount of the compound of Formula I, Compound 12, or Compound 19 or a pharmaceutical composition comprising the compound of Formula I, Compound 12, or Compound 19.

The present application provides a method of treating hyperglycemia in a patient comprising administering to a patient in need thereof an effective amount of the compound of Formula I, Compound 12, or Compound 19 or a pharmaceutical composition comprising the compound of Formula I, Compound 12, or Compound 19. The present application also provides a compound of Formula I, Compound 12, or Compound 19 for use in therapy. The present application further provides a compound of Formula I, Compound 12, or Compound 19 for use in the treatment of diabetes or the treatment of hyperglycemia.

The present application provides a compound, Compound A, having the formula:

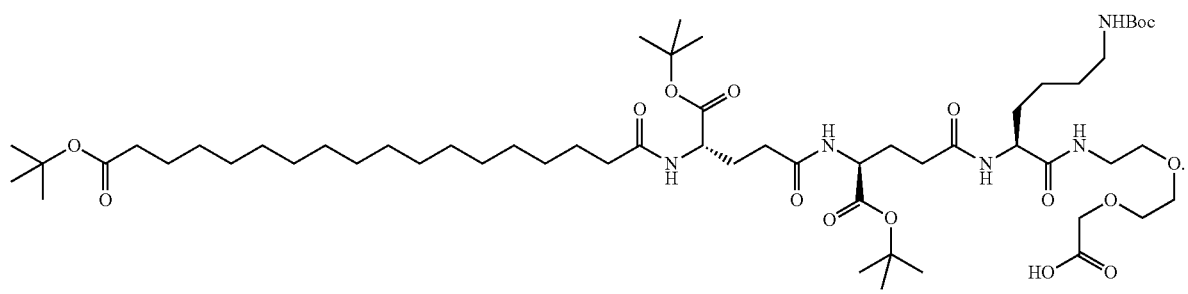 [SMILES: CC(C)(C)OC(=O)CCCCCCCCCCCCCCCCC(=O)N[C@@H](CCC(=O)N[C@@H](CCC(=O)N[C@@H](CCCCNC(=O)OC(C)(C)C)C(=O)NCCOCCOCC(=O)O)C(=O)OC(C)(C)C)C(=O)OC(C)(C)C]

The present application also provides the use of Compound A in the manufacture of a medicament for the treatment of diabetes and/or hyperglycemia. The present application further provides the use of Compound A in the preparation or manufacture of a compound of Formula I, Compound 12, or Compound 19.

Compounds of the present invention have a slower clearance rate than known acylated insulins, such as insulin degludec, which could improve bioavailability, achieve a more stable pharmacokinetic profile in humans over time and/or increase the duration of action of the compound in vivo. Also, compounds of the present invention exhibit a low chemical degradation rate, which indicates that they have increased chemical stability, and could achieve a shelf-life longer than known acylated insulins, such as insulin degludec.

The term "treatment" or "treating" as used herein refers to the management and care of a patient having diabetes or hyperglycemia, or other condition for which insulin administration is indicated for the purpose of combating or alleviating symptoms and complications of those conditions. The patient to be treated is an animal, and preferably a human being.

As used herein, the term "effective amount" refers to the amount or dose of a compound of the present invention or a pharmaceutical composition containing a compound of the present invention, which upon single or multiple dose administration to the patient or subject, will elicit the biological or medical response of or desired therapeutic effect on a tissue, system, animal, mammal or human that is being sought by the researcher, veterinarian, medical doctor or other clinician. A dose can include a higher initial loading dose, followed by a lower dose.

The terms "patient," "subject," and "individual," used interchangeable herein, refer to an animal, preferably the terms refer to humans. In certain embodiments, the patient, preferably a human, is further characterized with a disease or disorder or condition that would benefit from lowering glucose levels in the blood.

Pharmaceutical compositions comprising the compound of the present invention may be administered parenterally to patients in need of such treatment. Parenteral administration may be performed by subcutaneous, intramuscular or intravenous injection by means of a syringe, optionally a pen-like syringe, or mechanical driven injector. Alternatively, parenteral administration can be performed by means of an infusion pump.

Embodiments of the present invention provide pharmaceutical compositions suitable for administration to a patient comprising administering to a patient in need thereof a therapeutically effective amount of a compound of the present invention and one or more pharmaceutically acceptable excipients. Such pharmaceutical compositions may be prepared by any of a variety of techniques using conventional excipients for pharmaceutical products that are well known in the art. (Remington's Pharmaceutical Sciences, 21st Edition, University of the Sciences in Philadelphia, Philadelphia, Pa., USA (2006)).

The claimed compounds may be used in simultaneous, separate or sequential combination with one or more additional therapeutic agents useful for treating diabetes and/or conditions related to diabetes. Non-limiting examples of the additional therapeutic agents that can be combined with the claimed compounds include: insulin or insulin analogs; biguanides; sulfonylureas; thiazolidinediones; dipeptidyl peptidase-4 ("DPP-4") inhibitors; sodium-dependent glucose transporter (SGLT2) inhibitors; incretin compounds such as glucagon-like-peptide-1 (GLP-1) or GLP-1 analogs, gastric inhibitory polypeptide (GIP) or GIP analogs, oxyntomodulin or oxyntomodulin analogs; or combinations of any of the foregoing agents. The claimed compounds and the additional therapeutic agent(s) can be administered either together through the same delivery route and device such as a single pill, capsule, tablet, or injectable formulation; or separately administered either at the same time in separate delivery devices or routes; or administered sequentially.

One of the claimed acylated insulin compounds, Compound 12, was generated by selective acylation of the LysB29 epsilon amino group of A21G-insulin (human insulin wherein the 21$^{st}$ amino acid of the insulin A chain is substituted with Glycine, A21G-insulin) with the linker-fatty acid intermediate: C18-OtBu-γGlu(OtBu)-γGlu(OtBu)-Lys(Boc)-AEEA-OH, where C18-OtBu is 18-tert-butoxy-18-oxo-octadecanedioic acid, γGlu is L-glutamic acid connected through its side-chain gamma carboxyl group, and AEEA is 2-[2-(2-aminoethoxy)ethoxy]acetic acid.

Generation of the molecule occurred in three main stages: 1) generation of A21G-insulin, 2) synthesis of the linker-fatty acid intermediate, and 3) acylation, deprotection, purification and salt exchange to isolate Compound 12.

The insulin portion of the present compounds may be prepared by a variety of techniques known to one of skill in the art such as via production of a precursor protein molecule using recombinant DNA techniques. The DNA, including cDNA and synthetic DNA, may be double-stranded or single-stranded. The coding sequences that encode the precursor protein molecule described herein may vary as a result of the redundancy or degeneracy of the genetic code. The DNA may be introduced into a host cell in order to produce the precursor protein of the present invention. An appropriate host cell is either transiently or stably transfected or transformed with an expression system for producing the precursor protein. The host cells may be bacterial cells such as K12 or B strains of *Escherichia coli*, fungal cells such as yeast cells, or mammalian cells such as Chinese hamster ovary ("CHO") cells.

The expression vectors are typically replicable in the host organisms either as episomes or as an integral part of the host chromosomal DNA. Commonly, expression vectors will contain selection markers, e.g., tetracycline, neomycin, and dihydrofolate reductase, to permit selection of those cells transformed with the desired DNA sequences.

The present compounds may be prepared by a variety of procedures known in the art, as well as those methods described below. The specific synthetic steps for each of the routes described may be combined in different ways to prepare the compounds described herein. Compound 19 was prepared in a manner similar to that of Compound 12.

The linker fatty acid molecule portion of Compounds 12 and 19, having the formula shown below, Compound A, is generated using solid-phase synthesis as shown in the following schematic representation.

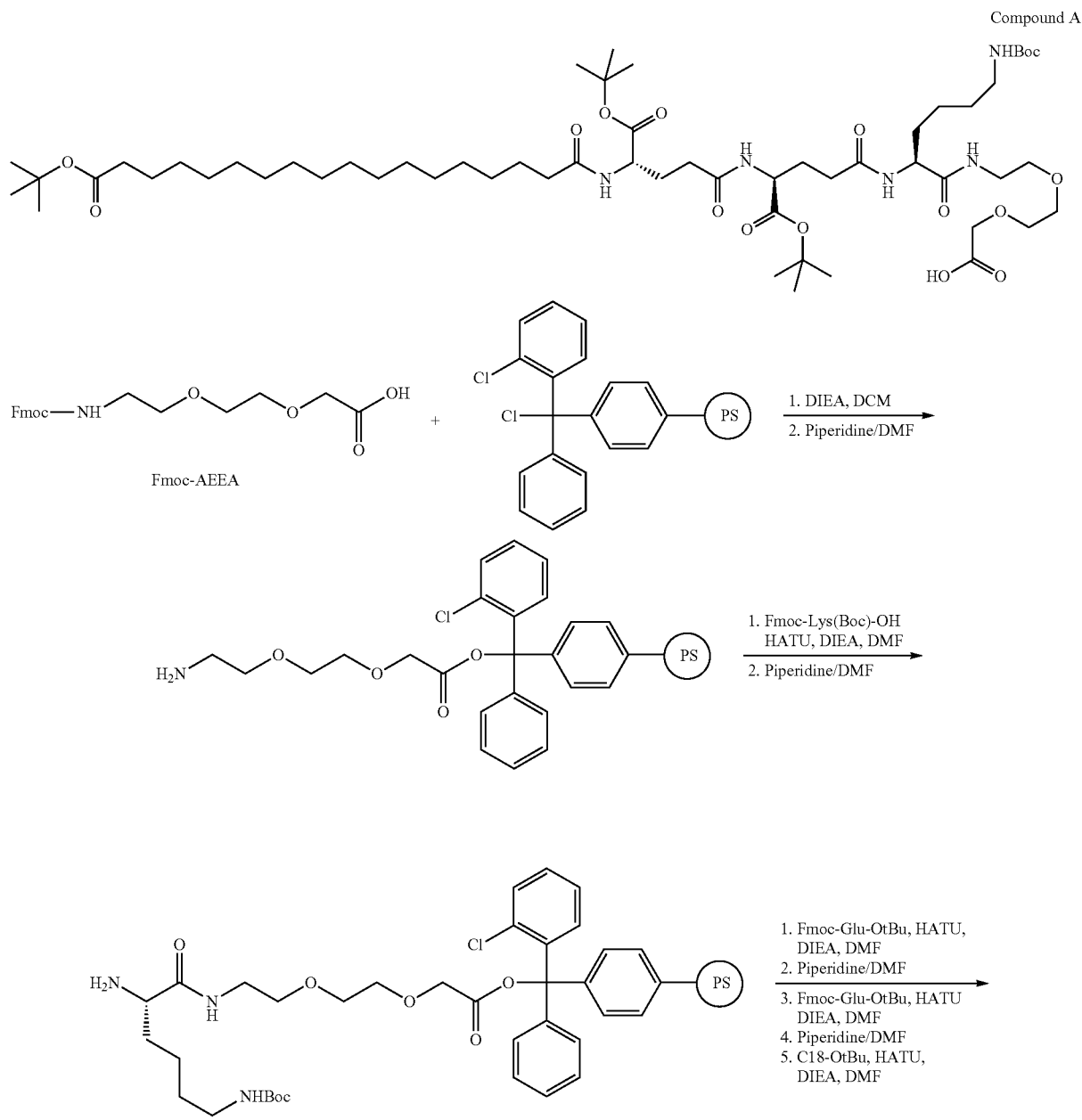

-continued

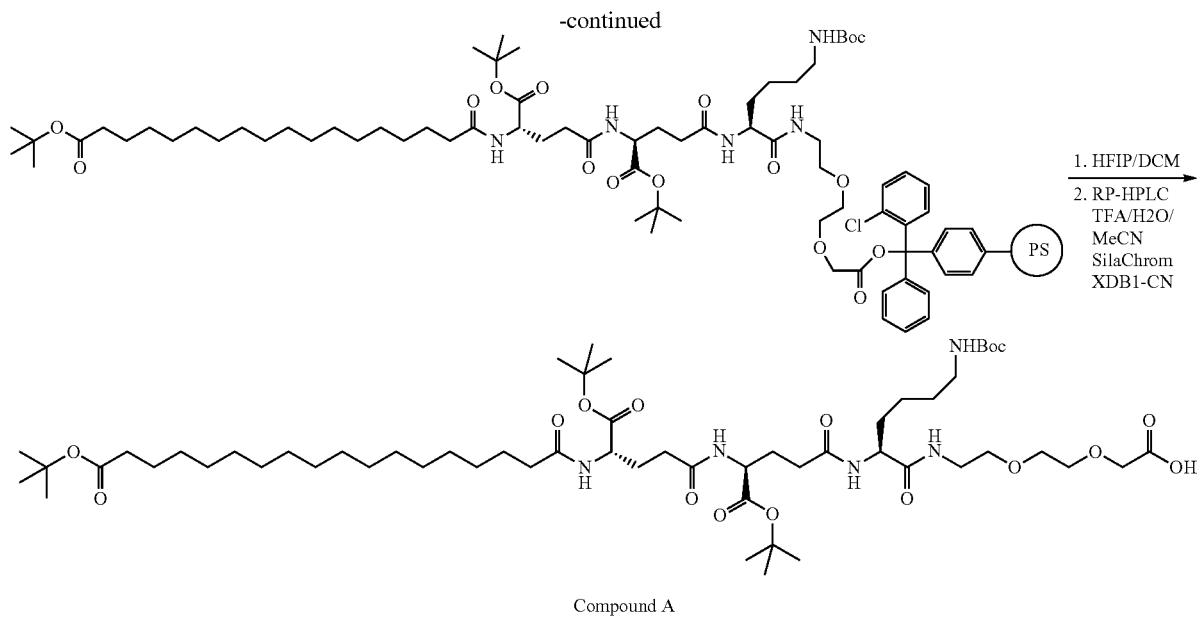

Compound A

Schematic Representation of the Synthesis of Compound A

"PS" Indicates Polymer Support

There is potential to generate Compound A using solution phase methods only or in combination with solid-phase methods which may be more scalable. Conjugation of the linker fatty acid molecule to A21G-insulin is performed in an organic solvent (N-methyl-2-pyrrolidone (NMP)/dimethyl sulfoxide (DMSO)) due to the solubility of the tert-butyloxycarbonyl "Boc"/tert-butyl esters "tBu" protected amino acid-based linker fatty acid. However, alternate protection/deprotection schemes could be devised to render the linker fatty acid soluble in aqueous solution to minimize the use of organic solvents.

Likewise, the last chemical transformation removes the Boc/tBu protecting groups using trifluoroacetic acid (TFA). An alternate protection/deprotection strategy could be devised for milder cleavage conditions.

Compound A is generated by solid-phase peptide synthesis. Fluorenylmethyloxycarbonyl (Fmoc)-Lys(Boc)-OH (1430 mg, 3 mmol, 2eq rel to resin; Novabiochem catalog#852012) is mixed with 1-[Bis(dimethyl amrnino)methylene]-1H-1,2,3-triazolo[4,5-b]pyridinium 3-oxid hexafluorophosphate (HATU) (1150 mg, 3 mmol, 2eq rel to resin; Oakwood Chemical catalog#023926) and N,N-Diisopropylethylamine (DIEA) (1333 ul, 7.6 mmol, 5 eq.) in 10 mL DMF for 2 minutes and then transferred to the vessel containing H-AEEA-2-chlorotrityl-chloride resin (2.11 g, 0.72 mmol/g, 1.52 mmol; Peptides International catalog# RHX-11074-PI), which is pre-swelled in dichloromethane (DCM) and pre-washed with dimethylformamide (DMF).

The slurry is mixed for 1.5 h, filtered and the resin is washed well with DMF (Kaiser test is negative). The Fmoc protecting group is removed by treatment of the resin with 20% piperidine/DMF (10 mL, 30 min). After a DMF wash of the resin (40 mL), the Kaiser test is positive to provide $H_2N$-Lys(Boc)-AEEA-2-chlorotrityl-chloride resin (1.52 mmol in theory).

Fmoc-Glu-OtBu (1297 mg, 3.0 mmol, 2.0 eq, Ark Pharma catalog# AK-48532) is pre-activated (2 min) with HATU (1153 mg, 3 mmol, 2 eq) using DIEA as base (1333 μL, 7.7 mmol, 5.0 eq) in 10 mL DMF, then transferred to the resin. The slurry is mixed for 3 hours, filtered, and the resin washed well with DMF (Kaiser test is negative).

The Fmoc protecting group is removed by treatment of the resin with 20% piperidine/DMF (10 mL, 30 min) followed by a DMF wash of the resin (40 mL, Kaiser test is positive). A second Fmoc-Glu-OtBu is coupled to the resin by repeating the conditions above using a 1.5 hour coupling time.

After removing the last Fmoc protecting group, 18-tert-butoxy-18-oxo-octadecanedioic acid (1.13 g, 3.0 mmol, 2.0 eq) is pre-activated (2 min) with HATU (1.15 g, 3.0 mmol, 2.0 eq) using DIEA as base (1333 L, 7.7 mmol, 5.0 eq) in 10 mL DMF, then transferred to the resin. The slurry is mixed for 3 hours, filtered, and the resin washed well first with DMF and then with DCM (Kaiser test is negative). The protected linker-fatty acid is cleaved from the resin by mixing with 30% HFIP/DCM (20 mL) for 1 hour. The resin is filtered off and rinsed well with DCM. The combined filtrates are evaporated to an oil in vacuo. The residual oil is diluted with acetonitrile (15-20 mL) and evaporated in vacuo again to an oil.

The sample is again dissolved with acetonitrile (15-20 mL) and is evaporated in vacuo to form an oil. A gentle stream of nitrogen evaporates the residual acetonitrile to give 2.6 grams of crude, amorphous solid (theory=1.7 grams).

Purification begins with the crude sample being dissolved in 5 mL DMF and 20 mL acetonitrile (including washes of flask). Then water is added to give 40 mL of a hazy solution. 5 mL additional acetonitrile gives a clear solution (total volume equaled 45 mL (33% aqueous). Purification is performed by loading the sample onto a semi-prep cyano reversed phase HPLC column (SilaChrom XDB1-CN; 10 m, 100 Å; 2.1×25 cm).

The sample is then eluted using a 40-60% B gradient over 72 min, 15 mL/min, 60° C. (buffer A=0.1% TFA in water and buffer B=0.1% TFA in acetonitrile). Fractions determined to contain the desired product by analytical RP-HPLC are pooled and lyophilized to give 1.22 grams of product (Compound A) as a white amorphous solid (72% of theory; 91% purity by RP-HPLC; obs MW=1114.6 Daltons (Da); theo MW=1114.45 Da).

Acylation begins with 404.9 mg; 0.363 mmol; 1.32 equivalents of Compound A, synthesis described above, and TSTU (O—(N-Succinimidyl)-N,N,N',N'-tetramethyluronium tetrafluoroborate) (91.5 mg 0.3039 mmol; 1.1 equiv), which are dissolved in 2.5 mL of N-methyl-2-pyrrolidone (NMP). To this solution is added diisopropylethylamine (DIEA, 192 μL; 1.102 mmol; 4 equiv), and the resulting mixture is incubated at room temperature for 30 minutes to generate the Compound A-OSu ester in NMP and used directly.

In creating Compound 12, to a solution of A21G-insulin (or to a solution of human insulin in the case of Compound 19) (TFA salt; 1.584 g; 0.276 mmol) dissolved in 15 mL of dimethyl sulfoxide (DMSO) is added 1,8-Diazabicyclo [5.4.0]undec-7-ene (DBU; 495 μL, 3.31 mmol, 12 eq., Sigma-Aldrich catalog#: 33482). Then, immediately, the above Compound A-OSu ester in NMP is added.

After the reaction mixture is stirred at ambient temperature for 12 minutes, it is added into a mixture of diethyl ether/DCM/TFA (30:10:0.2 v/v; 200 mL volume). The resulting white precipitate is isolated by centrifugation and then triturated with diethyl ether once.

Deprotection (removal of Boc and OtBu groups) begins with the above ether-wet white precipitate being treated with a mixture of TFA/triisopropylsilane (TIS; Aldrich)/water (92.5:5.0:2.5 v/v; 50 mL) for 20 minutes. To the mixture is added diethyl ether (200 mL) and the resulting precipitate is collected by centrifugation. RP-HPLC analysis shows the deprotection step to be complete (12.4% un-reacted A21G-insulin 56.7% B29-acylated product; 13% bis-acylated product).

Purification begins with the above crude product being dissolved in water/acetonitrile (1:1 v/v; 20 mL). Residual ether is removed by applying a gentle stream of nitrogen over the surface of the mixture until the volume was approximately 20 mL. The resulting solution is diluted with Milli-Q water (200 mL) and loaded onto a Zeosphere 120DRP, A10, C8 preparative HPLC column (5×25 cm). The sample is eluted from the column with a gradient of acetonitrile (20-35%) in water (containing 0.1% v/v TFA) over 144 minutes at 28 mL/min while UV monitoring at 225 nm and 280 nm. Fractions containing the desired product are identified by RP-HPLC (column: Waters XSelect CSH C18, 4.6×50 mm) and pooled (100 mL; 99.8% by RP-HPLC). ESMS: deconvoluted spectrum: observed: 6,577.1 Da; calc: 6,578.5 Da.

In the conversion to HCl salt exchange (column method), the above pooled fractions are diluted with water to 200 mL and reloaded onto the Zeosphere preparative HPLC column. The elution buffers are then changed. The A buffer contained 0.01% HCl in water and the B buffer is acetonitrile.

The column is then washed with three column volumes of 5% buffer B and then the sample is eluted using 70% buffer B while monitoring 225 nm and 280 nm. The sample is collected into a clean lyophilization jar, frozen and lyophilized to yield Compound 12 as a white powder (620.5 mg, 0.094 mmol; 34% overall yield). Purity is confirmed by analytical RP-HPLC and found to be 99.9%. ESMS: deconvoluted spectrum: observed: 6,577.3 Da; calc: 6,578.5 Da.

In the conversion to HCl salt exchange (resin method), Compound 12 (TFA salt; 102.9 mg) is dissolved in water/acetonitrile (1:1 v/v; 20 mL) and added to the chloride ion-exchange resin (4.05 g; 248 mmol of resin/mmol of insulin; Bio-Rad 1-x8 (cat#140-1431); 50-100 mesh; chloride form; 2.08 meq./dry gram; 46% moisture; quaternary ammonium; control number 2100011742) which is pre-washed with 20 mL each of methanol, acetonitrile, and water/acetonitrile (1:1 v/v).

The resin and the insulin are mixed at room temperature for 1 hour at which point the resin is filtered off and washed with water/acetonitrile (1:1 v/v, 20 mL). The filtrate and the washes are combined, frozen and lyophilized to yield Compound 12 as a white powder (89.9 mg; 87% step recovery). Purity is confirmed by analytical RP-HPLC and is found to be 99.9%. ESMS: deconvoluted spectrum: observed: 6576.7 Da; calc: 6578.5 Da. Additional methods of salt exchange may also be used, such as dialysis.

LysB29 acylation for the present compounds is confirmed by digestion with endoprotease Glu-C. Approximately 300 μg of Compound 12 or 19 is dissolved in 50 mM Tris buffer, pH 8 (1 mg/ml) and then treated with 20 μg endoprotease Glu-C (Worthington Biochemical Catalog# LS003605). After incubation at room temperature for 17.5 hr, an aliquot (200 μL) of the reaction mixture is quenched with 0.1N HCl (300 μL).

The resulting mixture (80 μL) is analyzed by LC/MS (Waters XBridge C8 column, 4.6×150 mm, 5 m, 130 Å). The diagnostic fragment, B22-30+Compound A, was found to be 1944.4 Da (vs. calc=1944.3 Da). All other resulting Glu-C digestion fragments of Compounds 12 or 19 were free of acylation.

In Vitro Receptor Affinity

Compounds 12 and 19 and control compounds (biosynthetic human insulin, and insulin-like growth factor 1 (IGF-1)) are tested in human insulin receptor (hIR) and human IGF-1 receptor (hIGF-1R) scintillation proximity assay (SPA) competitive radioligand binding assays using membranes prepared using differential centrifugation steps from stably-transfected 293 HEK cells overexpressing the recombinant hIR-A, hIR-B or hIGF-1R.

Assay buffer conditions are used consisting of 50 mM Tris-HCl, pH 7.5, 150 mM NaCl, 0.003% (w/v) NP-40 and containing either human recombinant (3-[$^{125}$I]-iodotyrosyl-A$^{14}$)-insulin or human recombinant [$^{125}$I]-IGF-1. Counts per minute (CPM) data is normalized to unlabeled human insulin or IGF-1 controls and plotted as percent inhibition on the y-axis versus log compound concentration on the x-axis. IC50 values are determined from 4-parameter logistic non-linear regression analysis (GeneData, Version 12) and represent the concentration at which specific binding was inhibited by 50%. If necessary, curve top or bottom parameters are fixed to 100 or 0 percent, respectively, to generate a complete curve.

The affinity constant (Ki) is calculated from the IC50 value based upon the equation $Ki=IC50/(1+L*/Kd)$ where L* equals the concentration of radioligand used in the experiment and Kd equals the equilibrium binding affinity constant of the radioligand for the respective receptor, determined from saturation binding analysis.

The calculated Ki values of Compound 12 are Ki=7.11 nM for hIR-A and Ki=7.56 nM for hIR-B (Table 1). Compound 12 and human insulin both have a binding affinity for hIR-A and hIR-B that is less than 10 nM and Compound 12 is highly selective for hIR-A and hIR-B compared to hIGF-1R (>500-fold selective for both), which is similar to the selectivity ratio of human insulin in the same assays.

The calculated Ki values of Compound 19 are Ki=3.40 nM for hIR-A and Ki=3.45 nM for hIR-B (Table 1). Compound 19 and human insulin both have a binding affinity for hIR-A and hIR-B that is less than 4 nM and Compound 19 is highly selective for hIR-A and hIR-B compared to hIGF-1R (>700-fold selective for both), which is more selective than the selectivity ratio of human insulin in the same assays.

TABLE 1

Human Insulin Receptor Subtypes A and B (hIR-A and hIR-B) and Human Insulin-like Growth Factor-1 Receptor (hIGF-1R) Binding Affinity, Ki and SEM values are geometric means expressed to 3 significant digits

| Name | $K_i$, nM (geoSEM, n) | | |
|---|---|---|---|
| | IR-A | IR-B | IGF-1R |
| Compound 12 | 7.11 (0.48, n = 3) | 7.56 (0.72, n = 3) | 4060 (582, n = 3) |
| Compound 19 | 3.40 (1.44, n = 6) | 3.45 (0.479, n = 3) | 2540 (462, n = 3) |
| Human insulin | 0.197 (0.012, n = 3) | 0.257 (0.030, n = 3) | 97.8 (10.3, n = 3) |
| IGF-1 | 5.40 (0.59, n = 3) | 65.9 (8.8, n = 3) | 0.157 (0.010, n = 3) |

Receptor Functional Activation

The insulin receptor contains an intracellular tyrosine kinase domain that upon ligand binding auto-phosphorylates its own tyrosine residues to allow recruitment of adaptor proteins that act to induce the insulin signaling pathways. Functional cellular activity for stimulation of receptor auto-phosphorylation on tyrosine residues is determined after ligand treatment of 293HEK cells over-expressing hIR-A, hIR-B, or hIGF-1R, each with a C-terminal C9 epitope (TETSQVAPA, SEQ ID NO: 5).

After stimulation of cells with various concentrations of ligand, in a medium devoid of albumin, at 37° C. for 60 minutes (hIR-A and hIR-B assays) or for 30 minutes (hIGF-1R assay), the level of tyrosine auto-phosphorylation by the kinase domain of each receptor is determined by ELISA; wherein, the activated receptor is captured by an antibody (RHO 1D4) to the C9 epitope tag, followed by detection of the level of tyrosine phosphorylation with the pan anti-phosphotyrosine horse radish peroxidase conjugate, 4G10™-HRP antibody.

Functional potency is reported as the concentration eliciting a half-maximal response (EC50) relative to a maximally efficacious concentration (100 nM) of the positive control, human insulin (hIR-A and hIR-B phosphorylation assays) or 10 nM of the positive control hIGF-1 (hIGF-1R phosphorylation assay). EC50 values are determined from 4-parameter logistic non-linear regression analysis (NGR Screener 13). If necessary, curve top or bottom parameters are set to 100 or 0, respectively.

Reported values for EC50 are shown as geometric mean and the geometric standard error of the mean (geoSEM), with the number of independent determinations indicated by "n" (Table 2).

Compound 12 demonstrates activation of human IR-A and IR—B isoforms. The potency of Compound 12 and human insulin for the IR-A and IR—B isoforms is under 40 nM. Compound 12 is about 1300 times more potent at hIR-A and hIR-B than IGF-1R, which is greater than the selectivity ratio of human insulin in the same assays.

Compound 19 demonstrates activation of human IR-A and IR—B isoforms. The potency of Compound 19 and human insulin for the IR-A and IR—B isoforms is under 25 nM. Compound 19 is about 400 times more potent at hIR-A and hIR-B than IGF-1R, which is greater than the selectivity ratio of human insulin in the same assays. By comparison, the selectivity of human insulin for IR-A and IR-B compared to IGF-1R is approximately 200-fold.

TABLE 2

Human Insulin Receptor Subtypes A and B (hIR-A and hIR-B) and Human Insulin-like Growth Factor-1 Receptor (hIGF-1R) Activation

| Name | $EC_{50}$, nM (geoSEM, n) | | |
|---|---|---|---|
| | IR-A | IR-B | IGF-1R |
| Compound 12 | 34.1 (2.5, n = 7) | 37.9 (3.2, n = 3) | 49900 (17300, n = 4) |
| Compound 19 | 23.4 (6.34, n = 7) | 13.7 (1.47, n = 3) | 7170 (1940, n = 7) |
| Human insulin | 1.53 (0.11, n = 7) | 1.83 (0.07, n = 3) | 351 (110, n = 4) |
| IGF-1 | 116 (11, n = 3) | 427 (29, n = 3) | 0.939 (0.146, n = 4) |

Evaluation of In Vivo Potency in a Rat Model of Type 1 Diabetes

The effects of Compounds 12 and 19 are investigated in streptozotocin (STZ)-treated rat diabetes model. Male Sprague-Dawley rats, 400-425 gram body weight, are obtained from Envigo, Indianapolis, Ind. After acclimation for approximately one week, the rats are anesthetized with isoflurane and given a single injection of Zanosar® (item #89256, Teva Parenteral Medicines, 40 mg/kg, IV). The rats are used in studies 3 days after injection of Zanosar; only animals with non-fasted blood glucose between 400-550 mg/dl are used in these studies.

The rats are distributed into groups to provide comparable variance in blood glucose and body weight; rats are randomized. The blood glucose is measured using Accu-Chek Aviva glucometer (Roche).

The STZ-treated rats are given a single subcutaneous (SC) dose of test article or vehicle (Sterile Normal Saline, 0.9% w/v sodium chloride solution). Blood samples for glucose measurements are collected by tail bleed. The animals have free access to food and water throughout the experiment. Plasma samples from these studies are sent for analysis of compound levels. As shown in Table 3, Compound 12 had effective glucose lowering for at least 24 hours at a dose of 100 nmol/kg. Table 3 shows the values for Compound 19 at various time points during the evaluation. Compound 19 also had effective glucose lowering for at least 24 hours at a dose of 100 nmol/kg.

TABLE 3

Compound 12 in vivo Potency

| Time (Hours) | Vehicle | Compound 12 (12.5 nmol/kg) | Compound 12 (25 nmol/kg) | Compound 12 (50 nmol/kg) | Compound 12 (100 nmol/kg) |
|---|---|---|---|---|---|
| | | | Group Avg Glucose mg/dl ± SEM (n = 5) | | |
| 0 | 490 ± 2.78 | 508 ± 19.8 | 486 ± 16.4 | 501 ± 13.3 | 489 ± 6.10 |
| 1 | 504 ± 26.0 | 535 ± 25.9 | 499 ± 31.1 | 501 ± 21.8 | 414 ± 7.15 |
| 2 | 480 ± 16.3 | 496 ± 25.7 | 360 ± 48.1 | 384 ± 66.3 | 123 ± 9.29 |
| 4 | 512 ± 35.1 | 450 ± 21.0 | 249 ± 91.3 | 122 ± 33.8 | 84.9 ± 10.4 |
| 6 | 500 ± 34.3 | 393 ± 67.9 | 209 ± 82.6 | 74.5 ± 8.92 | 70.5 ± 6.36 |
| 8 | 498 ± 16.6 | 473 ± 45.5 | 308 ± 62.5 | 95.9 ± 20.7 | 73.0 ± 6.13 |
| 10 | 561 ± 18.5 | 527 ± 36.4 | 412 ± 55.3 | 121 ± 12.9 | 73.9 ± 11.3 |
| 12 | 584 ± 7.53 | 586 ± 12.0 | 513 ± 39.6 | 261 ± 36.3 | 84.9 ± 12.5 |
| 18 | 553 ± 18.3 | 532 ± 34.4 | 499 ± 25.9 | 420 ± 42.6 | 114 ± 15.8 |
| 24 | 488 ± 13.0 | 539 ± 18.2 | 481 ± 38.4 | 344 ± 66.2 | 162 ± 37.3 |
| 36 | 601* ± 0 | 591 ± 10 | 589 ± 8.41 | 598 ± 3.0 | 591 ± 8.80 |
| 48 | 508 ± 11.3 | 551 ± 18.4 | 517 ± 29.1 | 510 ± 25.7 | 504 ± 22.9 |
| 72 | 553 ± 8.79 | 564 ± 15.5 | 557 ± 23.6 | 555 ± 20.5 | 550 ± 23.4 |
| 36 hour AUC | 19300 ± 197 | 19100 ± 358 | 16500 ± 1096 | 12400 ± 831 | 7480 ± 488 |

*values above 601 are not measured because that is the high reading on the glucometer

TABLE 4

Compound 19 in vivo Potency

| Time (Hours) | Vehicle | Compound 19 (12.5 nmol/kg) | Compound 19 (25 nmol/kg) | Compound 19 (50 nmol/kg) | Compound 19 (100 nmol/kg) |
|---|---|---|---|---|---|
| | | | Group Avg Glucose mg/dl ± SEM (n = 5) | | |
| 0 | 510 ± 28.6 | 513 ± 10.0 | 520 ± 20.8 | 530 ± 15.1 | 546 ± 16.8 |
| 1 | 500 ± 24.5 | 545 ± 17.8 | 517 ± 25.5 | 544 ± 11.8 | 541 ± 23.1 |
| 2 | 522 ± 21.9 | 518 ± 21.2 | 367 ± 38.0 | 302 ± 58.4 | 242 ± 30.7 |
| 4 | 442 ± 26.4 | 292 ± 77.9 | 109 ± 25.7 | 100 ± 21.0 | 74.2 ± 4.00 |
| 6 | 404 ± 18.6 | 204 ± 67.6 | 81.8 ± 4.79 | 63.8 ± 7.15 | 59.7 ± 6.06 |
| 8 | 418 ± 36.9 | 230 ± 73.3 | 113 ± 14.5 | 73.0 ± 10.7 | 69.1 ± 5.59 |
| 10 | 443 ± 39.2 | 324 ± 77.9 | 224 ± 13.2 | 150 ± 46.5 | 63.8 ± 5.32 |
| 12 | 548 ± 27.6 | 595 ± 6.40 | 386 ± 30.1 | 157 ± 80.5 | 93.5 ± 20.3 |
| 18 | 546 ± 36.3 | 573 ± 9.04 | 513 ± 23.3 | 356 ± 102 | 97.7 ± 5.38 |
| 24 | 519 ± 24.8 | 553 ± 21.1 | 536 ± 24.4 | 503 ± 26.9 | 190 ± 59.8 |
| 36 | 600 ± 1 | 601* ± 0 | 590 ± 9.63 | 566 ± 30.9 | 576 ± 11.6 |
| 48 | 498 ± 20.4 | 550 ± 20.2 | 510 ± 19.3 | 537 ± 17.4 | 499 ± 27.5 |
| 72 | 549 ± 22.2 | 566 ± 18.0 | 566 ± 18.5 | 579 ± 16.2 | 591 ± 10.1 |
| 36 hour AUC | 18700 ± 471 | 18100 ± 718 | 154000 ± 240 | 12700 ± 1240 | 7840 ± 557 |

*values above 601 are not measured because that is the high reading on the glucometer Evaluation of Drug Clearance in a Pig Model of Type 1 Diabetes Diabetic (alloxan induced), castrated, male Yucatan miniature swine with previously fitted vascular access are placed into slings for restraint and have their vascular access ports accessed (equipped for blood sampling) and checked for patency. The animals are randomly placed into treatment groups and returned to their pens. After two baseline blood samples are collected (−30 and 0 min), the animals are injected with test article at 1.8 nmol/kg, subcutaneously in the flank (0 min) with an insulin syringe (0.3 ml ⁵/₁₆" needle). All study animals have ad libitum access to clean, fresh water throughout the remaining blood collection period.

Serial blood samples (2.0 mL each) are collected from each animal at the following time points: −30, 0 (just before dose) 1.5, 3, 6, 12, 18, 24, 36, 42, 48, 54, 60 and 72 hours following the subcutaneous dosing. All study animals are then food-fasted overnight and not fed again until after the 24 hr sample is collected. At that time, animals are fed 300 grams of S-9 diet and administered 0.2 U/kg Humalog. They are again food fasted until after the 60 hr sample is collected and then they receive 300 grams of S-9 diet and 0.2 U/kg Humalog. They return to their normal feed and maintenance insulin regime after the 72 hr samples collection.

Blood samples (anticoagulant: none [serum]) are maintained at ambient temperature for at least 30 minutes but no more than 2 hours to allow for clotting. Serum glucose concentrations are determined using an automated AU480 Clinical Chemistry Analyzer. An aliquot for PK is shipped for analysis.

Data are represented as mean+/−standard error of the mean (SEM) unless otherwise specified. Glucose change from baseline is calculated by subtracting the glucose value at each time point from the baseline glucose value. The baseline value is calculated from the average of −0.5 and 0 min glucose values. Samples for PK/PD are collected up to 72 hours post dose.

Pig plasma (K3EDTA) concentrations for Compound 12 are measured by LC/MS at Q2 Solutions (Ithaca, N.Y.). Compound 12 is immunoprecipitated (IP) from 100 µL plasma/serum aliquots using an anti-insulin-biotin monoclonal antibody (Fitzgerald #10R-I134E) and streptavidin-coated magnetic beads (Invitrogen M-280). Following wash steps, the insulin variants are eluted from the IP complexes with acidic acetonitrile (5:20:80 formic acid/acetonitrile/water).

Following elution, 10 L of the eluent are injected onto the mass spectrometer for LC/MS analysis. The LC/MS system is comprised of a Dionex 2D-nanoUPLC liquid chromatograph (NCS-3500RS) and a Thermo Q/Exactive Plus mass spectrometer.

Resolution is achieved by two dimensional chromatography using serial trap columns consisting of a Thermo micro-precolumn (160454) and an Acclaim PepMap-100 C18 column (0.3×5 mm, 5 µm dp), and a Thermo Easy Spray PepMap C18 analytical column (75 m×15 cm, 5 µm dp), both operated at 60° C.

The mass spectrometer is operated in positive ion, nanoESI (Easy Spray) mode, and the following precursor/product ion transitions are monitored for Compound 12: 1316.600→586.854. The assays are verified to measure the insulin variant concentrations over the range of 0.25 to 50 ng/mL.

The pharmacokinetics (PK) of Compound 12 are evaluated in diabetic-induced male Yucatan swine following single subcutaneous (SC) administrations of 1.8 nmol/kg of Compound 12. A sample of insulin degludec is prepared in a similar manner to Compound 12 and is used as a comparator in this study.

Some PK parameters of Compound 12 and insulin degludec are shown in Table 5. The clearance rate of Compound 12 is 2-3 times slower than the clearance rate of insulin degludec, which could lead to a flatter PK profile and increased duration of action for Compound 12 in vivo in humans.

19 mg/mL glycerol, 3.15 mg/mL m-cresol, and 4 zinc per insulin hexamer (molar basis), at pH 7.5. The targeted concentrations were U200 (200 units/mL, which is equivalent to 1.2 mM), U400 (2.4 mM), U600 (3.6 mM) and U800 (4.8 mM). The actual concentrations of the solutions were within 0.1 mM of the targeted concentration levels. Samples of the comparator, insulin degludec are prepared in the same manner as the samples of Compounds 12 and 19 for the stability studies.

For in-use stability studies, the samples are loaded into 3 mL, siliconized cartridges at fill volumes of approximately 1.5 mL. The cartridge plungers are positioned so as to eliminate head space in the cartridge. Cartridges are then placed at 30° C. The samples are subjected to "in-use" conditions by attaching a needle and ejecting 5-10 µL approximately every 2 days. Analysis by reverse-phase chromatography (RP-HPLC) and size exclusion chromatography (SEC) are performed on the samples at the initial time point and after various additional days of storage, as detailed in the tables below.

For static storage stability studies, the samples are loaded into 3 mL cartridges at fill volumes of 1.5 mL or 0.3 mL glass vials at fill volumes of approximately 0.2 mL. The cartridges or vials are then placed at 30° C. Analysis by reverse-phase chromatography (RP-HPLC) and size exclusion chromatography (SEC) are performed on the samples at the initial time point and after various additional days of storage, as detailed in the tables below.

The RP-HPLC parameters are as follows: (1) Instrument: LC with UV detector and column oven; (2) Column: SymmetryShield RP18 3.5 um PN186000179 SN01593-532014028; (3) Column temperature: 60° C.; (4) 4. Mobile phase: A=0.085% TFA in water, B=0.085% TFA in acetonitrile; and (5) the Gradient, with a flow of 0.9 mL/min, is as follows:

| Time (min) | % A | % B |
| --- | --- | --- |
| 0 | 90.0 | 10.0 |
| 3.00 | 90.0 | 10.0 |
| 3.10 | 70.0 | 30.0 |
| 6.10 | 70.0 | 30.0 |
| 36.10 | 40.0 | 60.0 |
| 36.20 | 5.0 | 95.0 |

TABLE 5

Mean PK Parameters of Compound 12 and insulin degludec in Male Diabetic-Induced Yucatan Swine Following Single Subcutaneous Doses

| Compounds | Dose (nmol/kg) | Stat | $T_{1/2}$ (hr) | $T_{max}$ (hr) | $C_{max}$ (pmol/L) | $AUC_{0-inf}$ (hr * nmol/L) | CL/F (mL/hr/kg) |
| --- | --- | --- | --- | --- | --- | --- | --- |
| Compound 12 | 1.8 | Mean | 15 | 10 | 2510 | 78.3 | 23.8 |
|  |  | SD | 3 | 8 | 692 | 17.4 | 4.64 |
| insulin degludec | 1.8 | Mean | 13 | 12 | 881 | 23.5 | 87.8 |
|  |  | SD | 3 | 10 | 314 | 8.30 | 39.8 |

Abbreviations:
$T_{1/2}$ = half-life,
$T_{max}$ = time to maximal concentration,
$C_{max}$ = maximal plasma concentration,
$AUC_{0-inf}$ = area under the curve from 0 to infinity,
CL/F = clearance/bioavailability
(N = 5 for Compound 12, N = 6 for insulin degludec)

Evaluation of Chemical Stability

Samples are prepared by dissolving freeze-dried powder of Compounds 12 and 19 in 20 mM NaOH at a target concentration of approximately 6 mM. This solution is then dialyzed against 10 mM Tris resulting in a stock concentration of 5.6 mM. This stock solution is then used to prepare solutions at the target concentrations containing 10 mM Tris, -continued

| Time (min) | % A | % B |
|---|---|---|
| 38.20 | 5.0 | 95.0 |
| 38.30 | 90.0 | 10.0 |
| 41.30 | 90.0 | 10.0 |

Concentration of Compound 12 from U200 to U800 had no appreciable effect on stability as determined by RP-HPLC or SEC. The chemical stability of Compound 12 in an in-use stability study at 30° C. (data through 110 days) is shown in Table 6. The chemical stability of Compound 12, Compound 19 and comparator insulin degludec, all at U200 concentration, in a static stability study, is shown in Table 7. The chemical stability of insulin degludec at 30° C. in a static stability study is shown in Table 8.

The average degradation rate of the main peak of Compound 12 at four different concentrations is 0.064% per week, shown in Table 6. This rate is 7-8 times lower than the degradation rate of the main peak of insulin degludec, which is 0.49%, shown in Table 8. Table 7 shows a direct comparison of U200 formulations of Compound 12, Compound 19 and insulin degludec at the same time points. In the direct comparison shown in Table 7, the degradation rate of Compound 12 is more than four times lower than insulin degludec and the degradation rate of Compound 19 is more than two times lower than insulin degludec. The lower chemical degradation rate exhibited by Compounds 12 and 19 may lead to increased shelf life of the present compounds.

TABLE 6

The percent main peak of Compound 12 at 30° C. as monitored by RP-HPLC

| Time (days) | U200 | U400 | U600 | U800 |
|---|---|---|---|---|
| 0 | 98.3 | 98.3 | 98.3 | 98.3 |
| 7 | 97.9 | 98.4 | 98.3 | 98.3 |
| 18 | 97.8 | 98.2 | 98.2 | 98.3 |
| 27 | 97.9 | 98.2 | 98.1 | 98.0 |
| 41 | 97.8 | 98.0 | 98.2 | 98.2 |
| 53 | 97.6 | 97.8 | 98.0 | 98.0 |
| 83 | 97.0 | 97.3 | 97.5 | 97.7 |
| 110 | 97.2 | 97.4 | 97.4 | 97.5 |
| Average degradation rate (%/wk) | | 0.064 | | |

TABLE 7

The percent main peak of Compound 12, Compound 19 and insulin degludec at 30° C. as monitored by RP-HPLC

| Time (days) | Compound 12 U200 | Compound 19 U200 | insulin degludec U200 |
|---|---|---|---|
| 0 | 98.3 | 98.9 | 97.8 |
| 7 | 97.4 | 97.9 | 96.9 |
| 28 | 97.3 | 98.3 | 95.4 |
| Degradation rate (%/wk) | 0.145 | 0.255 | 0.602 |

TABLE 8

The percent main peak of insulin degludec at 30° C. as monitored by RP-HPLC

| Time (days) | U200 insulin degludec |
|---|---|
| 0 | 94.4 |
| 7 | 93.2 |
| 14 | 93.5 |
| 21 | 92.6 |
| 28 | 91.8 |
| 42 | 90.1 |
| 56 | 90.9 |
| Average degradation rate (%/wk) | 0.49 |

Sequences

Generic structure of the A-Chain (SEQ ID NO: 1)
GIVEQCCTSICSLYQLENYCXaa
wherein Xaa at position 21 of SEQ ID NO: 1 is G or N.

A-Chain of Compound 12 (SEQ ID NO: 2)
GIVEQCCTSICSLYQLENYCG

A-Chain of Compound 19 (SEQ ID NO: 3)
GIVEQCCTSICSLYQLENYCN

B-Chain of Compounds 12 and 19 (SEQ ID NO: 4)
FVNQHLCGSHLVEALYLVCGERGFFYTPKT

C-terminal C9 epitope (SEQ ID NO: 5)
TETSQVAPA

We claim:
1. A compound having the formula:
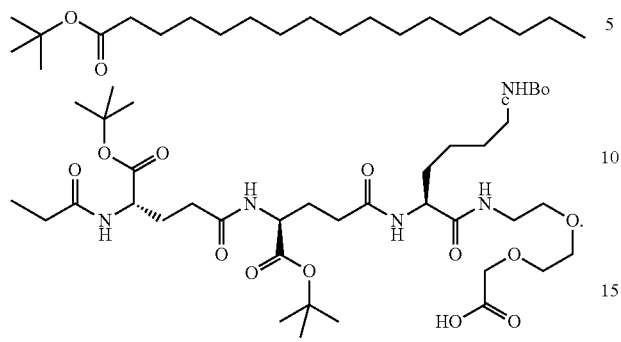
* * * * *

SEQUENCE LISTING

<160> NUMBER OF SEQ ID NOS: 5

<210> SEQ ID NO 1
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (6)..(11)
<220> FEATURE:
<221> NAME/KEY: MISC_FEATURE
<222> LOCATION: (21)..(21)
<223> OTHER INFORMATION: Xaa at position 21 is Gly or Asn

<400> SEQUENCE: 1

```
Gly Ile Val Glu Gln Cys Cys Thr Ser Ile Cys Ser Leu Tyr Gln Leu
1               5                   10                  15

Glu Asn Tyr Cys Xaa
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (6)..(11)

<400> SEQUENCE: 2

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 3
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (6)..(11)

<400> SEQUENCE: 3

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 4
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the Lys
      side-chain with OH-C18-gamma-Glu-gamma-Glu-Lys-AEEA-

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5

Thr Glu Thr Ser Gln Val Ala Pro Ala
1               5
```